United States Patent
Rousso et al.

(12)

(10) Patent No.: US 6,348,439 B1
(45) Date of Patent: Feb. 19, 2002

(54) HIGH ALKALINE HAIR COMPOSITIONS FOR INCREASED FULLNESS AND BODY

(75) Inventors: Peter J. Rousso, Trumbull; Paul S. Wallace, Cos Cob, both of CT (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/340,560

(22) Filed: Jun. 28, 1999

Related U.S. Application Data

(62) Division of application No. 09/035,397, filed on Mar. 5, 1998, now Pat. No. 6,010,990.

(51) Int. Cl.$^7$ .......................... A61K 7/075; C11D 17/00
(52) U.S. Cl. ....................... 510/125; 510/123; 510/124; 510/128
(58) Field of Search ................................ 510/128, 124, 510/125, 123, 127

(56) References Cited

U.S. PATENT DOCUMENTS

| | | | |
|---|---|---|---|
| 3,984,538 A | 10/1976 | Korkis | 424/74 |
| 3,988,438 A | 10/1976 | Weinstein | 424/70 |
| 4,076,800 A | 2/1978 | Marsh et al. | 424/70 |
| 4,140,759 A | 2/1979 | Mausner | 424/70 |
| 4,240,450 A | 12/1980 | Grollier et al. | 132/7 |
| 4,445,521 A | 5/1984 | Grollier et al. | 132/7 |
| 4,533,545 A * | 8/1985 | Sebag | 424/70 |
| 4,544,495 A * | 10/1985 | Schmolka | 252/174.21 |
| 4,604,282 A | 8/1986 | Grollier et al. | 424/74 |
| 4,719,099 A | 1/1988 | Grollier et al. | 424/47 |
| 4,800,080 A | 1/1989 | Grollier et al. | 424/74 |
| 4,830,784 A | 5/1989 | Meffert et al. | 252/547 |
| 4,847,076 A | 7/1989 | Deshpande et al. | 424/71 |
| 4,992,266 A * | 2/1991 | Knoll | 424/70 |
| 5,009,880 A | 4/1991 | Grollier et al. | 424/47 |
| 5,047,177 A | 9/1991 | Varco | |
| 5,202,048 A | 4/1993 | Bartolo et al. | |
| 5,288,484 A | 2/1994 | Tashjian | 424/71 |
| 5,352,389 A | 10/1994 | Gazzani | 252/544 |
| 5,358,667 A | 10/1994 | Bergmann | 252/547 |
| 5,393,305 A | 2/1995 | Cohen et al. | 8/406 |
| 5,456,863 A | 10/1995 | Bergmann | 252/547 |
| 5,523,017 A * | 6/1996 | Moran et al. | 252/174.21 |
| 5,612,024 A | 3/1997 | Giede et al. | 424/70.11 |

FOREIGN PATENT DOCUMENTS

| | | |
|---|---|---|
| EP | 0 018 717 | 11/1980 |
| WO | WO 97/35542 | 10/1997 |
| WO | WO 97/38672 | 10/1997 |
| WO | WO 98/04241 | 2/1998 |
| WO | WO 98/00486 | 10/1998 |

OTHER PUBLICATIONS

H. Edelstein, Apr. 1985, "Hair Conditioners and Conditioning", Cosmetics and Toiletries, vol. 100 (4): 31–36.

* cited by examiner

*Primary Examiner*—Yogendra N. Gupta
*Assistant Examiner*—John M. Petruncio
(74) *Attorney, Agent, or Firm*—Charles J. Zeller; Morton S. Simon

(57) ABSTRACT

The invention provides compositions for providing body, fullness and texture to otherwise fine or very fine keratinous fibers, particularly human hair. The compositions of the present invention have a high pH, e.g., about 8 to about 10 when the compositions contain cationic polymer, and a pH of about 8 to about 14, preferably about 8.5 to about 13, and more preferably, about 8.5 to about 10 when the compositions contain no cationic polymer. The compositions include one or more nonionic and/or cationic polymers, which, in combination with the high pH of the composition, lift the hair cuticle and allow the deposition of polymer, thus resulting in increased fullness and texture to the hair. The compositions of the present invention may be in the form of known hair care products such as, for example, shampoos, rinses and conditioners. In addition, the compositions can be formulated, for example, as lotions or creams, and the like, for consumer use. The hair care compositions of the present invention provide beneficial and long-lasting effects of body and fullness within a minute or less after application to the hair.

13 Claims, No Drawings

HIGH ALKALINE HAIR COMPOSITIONS FOR INCREASED FULLNESS AND BODY

This application is a divisional of U.S. patent application Ser. No. 09/035,397 filed Mar. 5, 1998 U.S. Pat. No. 6,010,990.

FIELD OF THE INVENTION

The present invention relates generally to hair shampoos and hair care products. More particularly, the invention relates to shampoo and hair care compositions having a high pH and comprising components which provide conditioning effects and increased body and fullness to the hair, particularly, fine hair or very fine hair.

BACKGROUND OF THE INVENTION

Hair care products specific to the needs of consumers with fine hair have long been commercially available. Shampoos for improving the body of fine hair have been the most widely used of all hair care products. Such shampoos that are common to the marketplace are typically formulated to have pH ranges that are acidic to neutral, for example, about 5.5 to 7.0. Many of the low pH to neutral pH hair shampoos do not provide lasting fullness and body to fine and very fine hair. This may be a consequence of a failure of prior art products to provide a perception of texture to the hair or to remain on the hair shaft after subsequent rinsing and shampooing.

Low pH works to close cuticles that surround the hair shaft. This, in turn, decreases penetration of active ingredients in a product and tends to decrease the diameter of the hair, thus resulting in a decrease in the perception of body and fullness of the hair.

U.S. Pat. Nos. 4,240,450; 4,445,521; 4,719,099 and 5,009,880 to J.-F. Grollier et al. disclose anchoring of anionic polymers to keratin material by means of a cationic polymer, via an interaction (i.e., complexation) between the two types of polymers. The Grollier et al. patents do not disclose or teach high pH and rapid deposition of polymer. The patents disclose that the substantivity of the anionic polymer is improved by its interaction with cationic polymer.

U.S. Pat. No. 4,847,076 to V. M. Deshpande et al. discloses compositions and methods for enhancing the body of hair in which harsh reducing agents, i.e., alkali metal or ammonium bisulfites, are required. The disclosed compositions require contact with hair for about 20 to 30 minutes prior to rinsing from the hair.

U.S. Pat. No. 5,352,389 to G. Gazzani discloses aqueous compositions for cleaning hair, skin and scalp. The disclosed compositions include surfactants and lipases to increase their cleaning efficacy. No polymers are included in the compositions, which are not contemplated for improving or providing long-lasting fullness and body.

H. Edelstein, "Hair Conditioners and Conditioning", *Cosmetics and Toiletries*, Vol. 100 (4):31–36, April 1985, discloses that cationic substances having a strong positive charge are attracted to the hair at pH above 3.8. However, there is no recognition that a cationic polymer in a composition at a pH from about 8 to about 10, or a nonionic polymer in a composition at a pH of from about 8 to about 14, results in an increased perception of texture, body and fullness to the hair by the user.

The present invention addresses the need in the art for improved shampoos and hair care products designed to increase fullness and body to hair, particularly fine and very fine hair. The present invention provides novel alkaline compositions and formulations, which combine a higher pH, i.e., about 8 to 8.5 and above, with cationic and/or nonionic polymers, to create products that provide, in a surprisingly short time, a perception of texture to the hair and impart long-lasting fullness and body to users with fine to very fine hair. The terms "high pH" and "high or highly alkaline" are used interchangeably herein.

SUMMARY OF THE INVENTION

It is an object of the present invention to provide hair care products for improving and adding fullness, texture and body to keratinous fibers, particularly human hair, and more particularly, fine or very fine hair. A variety of hair care products are intended to be embraced by the present invention, including, but not limited to, shampoos, conditioning shampoos and rinses.

It is another object of the present invention to provide high alkaline hair compositions and methods containing one or more nonionic and/or cationic polymers, for example, guars and the like, and derivatives thereof, wherein the compositions are stable and active over time, despite the higher pH environment of the composition. In accordance with the present invention, when the compositions contain a cationic polymer, the pH of the compositions is from about 8 to about 10; however, when the compositions contain no cationic polymer, the pH of the compositions can be from about 8 to about 14, preferably about 8.5 to about 13, and more preferably, about 8.5 to about 10. Also, in accordance with the present invention, the components of the hair compositions rapidly deposit on the hair to provide body, fullness and texture to otherwise fine or very fine hair, after shampooing and rinsing from the hair.

Further objects and advantages afforded by the present invention will be apparent from the detailed description hereinbelow.

DETAILED DESCRIPTION OF THE INVENTION

The present invention provides new compositions and formulations that are capable of imparting a noticeable increase in body and fullness to hair, particularly, fine and very fine hair. As used herein, the terms composition and formulation are interchangeable. The compositions of the present invention have a pH of about 8 or greater, and comprise one or more nonionic and/or cationic polymers, wherein the use of the products provides to the user the perception of fuller texture and body to the hair. The elevated pH combined with one or more nonionic and/or cationic polymers in the compositions of the present invention provide the effects of fullness, texture and body to the hair, along with conditioning effects, if desired, especially if a cationic polymer, such as guar, is included in the inventive compositions.

Without wishing to be bound by theory, it is believed that the elevated pH of the compositions of the present invention causes the hair or a shaft of a keratinous fiber to swell and the cuticle to lift. This effect is temporary; thus, when the hair is rinsed, the pH returns to normal or near-normal levels, and the cuticles flatten. However, in accordance with the present invention, the formulation of the polymers in a high pH medium, such as a shampoo, for example, allows the hair to swell and the included polymers to penetrate into the hair and to deposit under the cuticle and attach to the hair. The included nonionic and/or cationic polymers prevent the cuticle from closing completely, which thickens the hair shaft and provides it with more surface roughness and texture, after application to the hair. This effect was unexpectedly discovered by the present inventors to occur rapidly, i.e., within one minute or less.

As mentioned above, upon rinsing the hair and lowering the pH, the presence of the deposited polymer in the compositions of the present invention blocks the cuticle from returning to its prior flattened state. In accordance with the present invention, the polymer is trapped and the hair thus feels slightly "swelled". This imparts a thicker look and feel to the hair and gives the hair fiber more body and fullness.

The hair care compositions of the present invention are aqueous based and may be prepared in a variety of final formulations including lotions, creams, gels, emulsions, pumps, sprays, aerosols, mousses/foams, solutions and the like. Water is present in the compositions at about 30% to about 99%, preferably, about 50% to about 95%, more preferably, about 70% to about 90%, by weight, based on the total weight of the composition. It is hereinafter to be understood that, unless otherwise specified, all reagents and components of the compositions of the present invention are present in % by weight, based on the total weight of the composition.

In accordance with the present invention, when a cationic polymer is present the pH range of the shampoo and hair care product formulations of the present invention is about 8 to about 10; in the absence of a cationic polymer in the formulations, the pH range can be about 8 to about 14, preferably about 8.5 to about 13, and more preferably, about 8.5 to about 10.

The nonionic and cationic polymers suitable for use in the compositions of the invention provide the benefits of penetrating and thickening the hair, thereby preventing the collapse of the cuticles during rinsing and allowing polymer deposition on the surface of the hair to increase texture. Moreover, in the high pH environment of the compositions of the present invention, these polymers deposit and produce their beneficial effects within seconds, thus providing the compositions of the present invention advantages in time and efficiency.

Cationic polymers which can be used in the present invention include, but are not limited to, polymers having quaternary amine groups. More specifically, a cationic polymer for use in the present invention is a cationic derivative of guar gum or locust bean gum. Such gums are polygalactomannans containing two mannose units with a glycoside linkage and a galactose unit attached to one of the hydroxyl groups of the mannose units. The hydroxyl groups are reacted with certain reactive quaternary ammonium compounds to obtain the cationic derivative.

The quaternary ammonium compounds suitable for preparing the cationic gum derivatives of the present invention have the following structure:

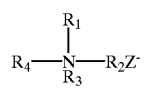

wherein $R_1$, $R_2$ and $R_3$ are alkyl, aryl and substituted alkyl and aryl groups, $R_4$ is selected from the group consisting of epoxyalkyl and halohydrin, and Z is an anion, e.g., Cl⁻, Br⁻, I⁻ and HSO4⁻. Suitable epoxyalkyl groups have the structure:

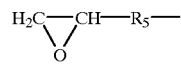

and suitable halohydrins have the structure:

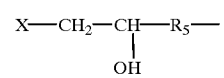

wherein $R_5$ is a divalent alkylene of 1 to 3 carbons and X is a halogen.

Particularly preferred is the compound 3-(trimethylamino)-2-hydroxypropyl guar chloride which has the structure:

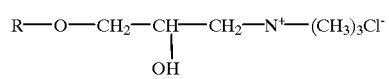

wherein R is a polygalactomannan molecule based on guar, and is sold as Cosmedia Guar 216N by Henkel Corporation. Another preferred cationic guar is a quaternary ammonium derivative of hydroxypropyl guar, such as guar hydroxypropyltrimonium chloride, which is exemplified by the JAGUAR® products commercially available from Rhone-Poulenc.

Nonionic polymers which are suitable for use in the present invention are generally classified as water soluble nonionic poly(ethylene oxide) homopolymers (e.g., polyethylene glycols) having the following structure:

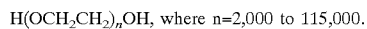

More specifically, the nonionic polymers include the Polyox® water soluble resins (Amerchol) which are completely water-soluble, are stable at pH of about 8 to 12 and range in molecular weight from approximately 100,000 to approximately $5 \times 10^6$. Nonlimiting examples of particular grades of polyethylene glycol (Polyox) water soluble resins suitable for use in the present invention are included in the following Table 1:

TABLE 1

| {PRIVATE}Tradename | CTFA Name |
|---|---|
| Polyox WSR N-10 (MW: 100,000) | PEG-2M |
| Polyox WSR N-80 (MW: 200,000) | PEG-5M |
| Polyox WSR N-750 (MW: 300,000) | PEG-7M |
| Polyox WSR N-3000 (MW: 400,000) | PEG-14M |
| Polyox WSR N-3333 (MW: 400,000) | PEG-9M |
| Polyox WSR 205 (MW: 600,000) | PEG-14M |
| Polyox WSR-1105 (MW: 900,000) | PEG-20M |
| Polyox WSR N-12K (MW: 1,000,000) | PEG-23M |
| Polyox WSR N-60K (MW: 2,000,000) | PEG-45M |
| Polyox WSR-301 (MW: 4,000,000) | PEG-90M |
| Polyox Coagulant (MW: 5,000,000) | PEG-115M |

Preferred is Polyox WSR N-750 (PEG-7M).

The polymers are present in the compositions in accordance with the present invention in an amount effective to increase hair body and fullness. More specifically, the polymers are present at about 0.01% to about 10%, preferably, about 0.05% to about 5% and more preferably, about 0.1% to about 1%.

In another embodiment of the present invention, one or more surfactants is included in the high pH compositions as described. Suitable surfactants are described below. Preferred surfactants in these compositions are anionic and/or amphoteric surfactants, and betaines. Nonlimiting examples of preferred surfactants include sodium lauryl sulfate, cocamidopropyl betaine (CAPB), sodium laureth sulfate and blends or mixtures thereof.

A preferred composition of the present invention comprises a high pH, e.g., about 8.0 to about 10, at least one cationic polymer and/or a nonionic polymer and one or more anionic surfactant. Preferred polymers in the compositions of the present invention include, but are not limited to, Jaguar® (Rhone-Poulenc), Polyox® (Amerchol), Celquats (National Starch), Merquats (Merck), Gafquats (ISP), Polymer JR (Amerchol) and Cosmedia Polymer LR (Henkel Corporation).

Suitable anionic surfactants for use in the compositions of the present invention are those generally incorporated into hair care products of the desired types. Generally, for shampoos, the anionic surfactants are water-soluble alkyl or alkyl aryl sulfates or sulfonates having from about 8 to about 22 carbons, preferably from about 12 to about 18 carbons in the alkyl radical, which may be straight or branched chain. These surfactants also include such classes of compounds which are ethoxylated with from 1 to 5 mols, preferably 1 to 3 mols, of ethylene oxide (EO) per molecule. The sulfate or sulfonate group is typically base-neutralized to provide an alkali metal, especially a sodium, potassium, ammonium, or mono-, di- or triethanolamine.

Illustrative anionic surfactants of the above-named classes include, but are not limited to: sodium cetyl sulfate; sodium myristyl sulfate; sodium lauryl sulfate; sodium tallow sulfate; sodium decyl sulfate; sodium decylbenzene sulfonate; sodium tridecylbenzene sulfonate; sodium $C_{14}$–$C_{16}$ olefin sulfonate; sodium $C_{12}$–$C_{15}$ alcohol sulfate; sodium lauryl ether sulfate; sodium myristyl ether sulfate; sodium polyoxyethylene (5 mols EO) lauryl ether sulfate; sodium polyoxyethylene (12 mols EO) lauryl ether sulfate; sodium nonylphenyl ether sulfate; sodium polyoxyethylene (1 to 4 mols EO); $C_{12}$–$C_{15}$ alkyl ether sulfate and sodium lauryl sulfoacetate. Although sodium salts are identified above, the other, previously-named cations would also be suitable, especially ammonium.

Other suitable anionic surfactants include sulfosuccinates, e.g., sodium dioctyl sulfosuccinate; disodium lauryl sulfosuccinate and the disodium polyoxyethylene (1 to 4 mols EO) lauryl alcohol half ester of sulfosuccinic acid; sulfated monoglycerides, e.g., sodium cocomonoglyceride sulfate; sarcosinates, e.g., sodium cocoyl sarcosinate and sodium lauroyl sarcosinate; esters of isethionic acid, e.g., sodium cocoyl isethionate and sodium lauroyl isethionate; taurates, e.g., sodium N-methyl-N-cocoyl taurate and sodium N-methyl-N-oleoyl taurate. Soaps may also be incorporated, e.g., sodium stearate, sodium laurate and sodium isethionate. Also suitable are protalbinic and lysalbinic acid derivatives, generally classed as Maypon surfactants. The anionic surfactants may be used singly or in combination. Often, two or more anionic surfactants may be blended to achieve a desired viscosity, cleaning benefit, or other property.

The anionic surfactants are typically present in the compositions of the present invention in an amount of from about 1% to about 50% active. However, the concentration is not deemed critical so long as the concentration employed does not interfere in the physical stability of the product shampoo. Preferably, the anionic surfactants are present in an amount of from about 5% to about 35% active, most preferably, from about 10% to about 25% active.

Preferred anionic surfactants are sodium or ammonium $C_{12}$ to $C_{14}$ alkyl sulfates, and sodium or ammonium $C_{12}$ to $C_{14}$ alkyl ethyl sulfates having 1 to 3 mols EO. An especially preferred anionic surfactant system (e.g., a surfactant blend) comprises from about 4% to about 15% active sodium lauryl sulfate and from about 3% to about 10% active sodium lauryl ether sulfate.

Other types of surfactants can also be used in concert with anionic surfactants in the compositions of the present invention. Such surfactants include nonionic, betaines (a class of zwitterionic surfactants), amphoteric and cationic surfactants.

Suitable nonionics can be broadly defined as compounds produced by the condensation of alkylene oxide groups (hydrophilic in nature) with an organic hydrophobic compound, which may be aliphatic or alkyl aromatic in nature. Such nonionics are characterized by long chain oxyethylene or oxyethylene-oxypropylene units. Illustrative materials are the polyoxyethylene octyl and nonyl phenyl ethers having above about 6 mols ethylene oxide, preferably about 6 to 15 mols ethylene oxide, e.g., the Igepal surfactants; block copolymers of ethylene and propylene oxide generally designated as Pluronic® surfactants, and polyoxyethylene sorbitan monolaurates and monostearates, generally designated as Tween surfactants. However, these classes of nonionic surfactants are exemplary and should not be regarded as limiting. The nonionic surfactant is generally present in the compositions of the present invention in an amount of from about 0.1% to about 10%, preferably from about 0.1% to about 5%.

Betaines, a class of zwitterionic surfactants, are also suitable for use in the present invention. Examples of betaines that are useful herein include the high alkyl betaines, such as cocodimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, and the like. The sulfobetaines are illustrated by cocodimethylsulfopropyl betaine, stearyl dimethylsulfopropyl betaine, lauryl dimethylsulfoethyl betaine, lauryl bis-(2-hydroxyethyl) sulfopropyl betaine, and the like. Amido betaines and amidosulfobetaines, especially those wherein the RCONH$(CH_2)_3$ radical is attached to the nitrogen atom of the betaine, are useful in the present invention, for example, cocamidopropyl betaine.

Illustrative amphoteric surfactants which can be used in the compositions of the present invention are those which can be broadly defined as derivatives of aliphatic secondary and tertiary amines in which the aliphatic radical can be straight chain or branched chain, wherein one of the aliphatic substituents contains from about 8 to about 18 carbon atoms and one contains an anionic water solubilizing group, e.g., carboxy, sulfonate, sulfate, phosphate, or phosphonate. Particularly useful examples of amphoterics include sodium 3-dodecylaminopropane sulfonate, sodium 3-dodecylaminopropionate, disodium cocamphodiproprionate, disodium cocamphodiacetate, N-alkyl taurines, N-alkyl-β-imino dipropionates and the basic ammonium compounds derived from 2-alkyl-substituted imidazoline, e.g., Miranol surfactants, as described in U.S. Pat. No. 2,528,378. The above-listed amphoterics are not intended to be limiting.

The compositions of the present invention may also contain additive ingredients which improve, for example, the quality and elegance of the final products, as set forth below. These additional components are present at levels which are effective to provide their intended functions.

Foam builders or foam stabilizers are materials which increase the quality, volume and stability of the lather. They also enhance viscosity. Preferred foam builders are fatty acid alkanolamides, such as lauroyl diethanolamide, lauroyl monoethanolamide and coconut monoethanolamide. Other foam builders are "super" amides, e.g., Super amide B-5, fatty alcohols, sarcosinates, phosphates and dodecylbenzene sulfonates. The foam builders are typically present in an amount of from about 0.1% to 10%, preferably, from about 0.5% to about 5%.

Opacifying agents are used, for example, in cream compositions. Suitable opacifying agents are the higher alcohols, such as stearyl and cetyl alcohol, and the higher acids, such as behenic acid. The glycol mono- and di-stearates are also effective opacifiers. Alkaline earth metal fatty acid soaps, such as calcium stearate and magnesium stearate, are also suitable. Magnesium silicates are also useful for this purpose. Opacifying agents are typically present in an amount of from about 0.1% to about 10%, preferably, from about 0.5% to about 5%.

Viscosity-control agents are often useful to stably regulate the viscosity of the ingredients of a shampoo composition. Suitable viscosity-control agents are lower alcohols, e.g., isopropyl glycol and butyl alcohol; and lower glycols, e.g., diethylene glycol, terpineol and diethyl carbitol. These agents are typically present in an amount of from about 0.1% to about 5%, preferably, from about 0.5% to about 2.5%.

Sequestering agents are useful to prevent the formation of a lime soap film when shampooed hair is rinsed with hard water. Suitable materials are ethylenediaminetetraacetic acid (EDTA), citric acid, sodium xylene sulfonate and sodium naphthalene sulfonate. Sequestering agents are typically present in an amount of from about 0.01% to about 5%, preferably, from about 0.1% to about 1%.

Thickening agents increase the viscosity of a shampoo product. Suitable materials are natural gums such as tragacanth, xanthan, acacia and locus bean; and synthetic gums such as hydroxypropylcellulose and methyl cellulose. Polyvinyl alcohols can also be used. Alkanolamides (e.g., cocamide MEA and lauramide DEA), "super" amides and the glycol or glycerol stearates may also be used. Thickening agents are present in an amount to provide the desired viscosity, typically from about 0.1% to about 10%, preferably, from about 0.1% to about 10%.

Preservatives are typically present to prevent degradation from bacterial and mold action. Formaldehyde, methyl, ethyl, propyl and butylhydroxybenzoates, dimethyl dimethyl hydantoin, methylchloroisothiazolinone, methylisothiazolinone, 2-phenoxyethanol and mixtures thereof are preferred. They are present in compositions an amount of from about 0.01 to about 1%.

Cationic surfactants can also be employed in conjunction with the other ingredients, for example, to add conditioning properties to the compositions of the present invention. Nonlimiting examples of such cationic surfactants are represented by ricinoleamidopropyl ethyldimonium ethosulfate; quaternium 75, isostearamidopropyl ethyldimonium ethosulfate and linoleamidopropyl PG-dimonium chloride phosphate. Such cationics are generally present in the compositions in an amount to perform their intended function, i.e., about 0.1% to about 5%.

The amount of water employed in the formulation of the compositions of the present invention is generally the amount necessary to QS to 100%. However, it will be appreciated by those having skill in the art that in formulating the described compositions, the amount of water may require adjustment as necessary to insure that the final composition is stable in the sense of its being a homogeneous solution.

Other additives include antioxidants, such as sodium sulfite; propellants; suspending agents; fragrances and herbals; coloring agents; sunscreens; and buffering or pH control agents, such as citric acid, each of which is present in an amount, usually less than about 5%, effective to provide its intended function. An antidandruff component, e.g., selenium sulfide, may also be included at an effective level.

EXAMPLES

The following examples are meant to illustrate and exemplify the various aspects of carrying out the present invention and are not intended to limit the invention.

The compositions prepared as shampoos in accordance with the present invention were compared with other shampoo formulations having acidic pH (e.g., pH between about 5.0 and 6.0) and alkaline pH (e.g., pH between about 8.5 and 9.5) in consumer home usage studies.

Table 2 shows the results of the consumer usage studies in which the shampoo formulations as set forth in Examples 1–6 hereinbelow were tested.

For the consumer usage studies presented in Table 2, all of the test samples were placed in coded white plastic bottles and were labeled as "Shampoo for fine hair" with simple usage directions. The users in the home usage studies had self-perceived fine/very fine hair. They used the products as directed for two weeks and then responded to a call-back questionnaire.

It is to be understood that the term "body" as evaluated in the consumer usage studies includes both visual and tactile impressions or perceptions attributed to the hair by the user. Those skilled in the art will appreciate that an increase in hair "body" denotes to the user the overall impression or perception of a thicker or fuller feel, and/or manageability, and/or a thicker or fuller look to the hair.

Referring to the consumer usage test data of Table 2, Examples 1–3 are commercially available low pH (acidic) shampoo formulations for fine hair. They differ slightly in pH (due to normal, batch-to-batch pH variation). The Example 1 formulation contains no polymer; the Example 2 formulation contains a cationic polymer; and the Example 3 formulation contains a nonionic polymer. The consumer use test data show that no real differences in bodifying action were perceived between the acidic formulation of Example 1 containing no polymer and the acidic formulation of Example 3 containing a nonionic polymer.

In addition, a decrease in the overall opinion of the user is seen when the acidic formulation without polymer was compared with the acidic formulation with cationic polymer (i.e., 50% versus 40%, respectively).

Examples 4–6 are representative of the high pH (alkaline) shampoos for fine hair of the present invention. The formulation of Example 5 contains a cationic polymer; the formulation of Example 6 contains a nonionic polymer, while

TABLE 2

|  | ACIDIC FORMULATIONS | | | ALKALINE FORMULATIONS | | |
| --- | --- | --- | --- | --- | --- | --- |
| {PRIVATE} | Example 1 No Polymer | Example 2 Cationic Polymer | Example 3 Nonionic Polymer | Example 4 No Polymer | Example 5 Cationic Polymer | Example 6 Nonionic Polymer |
| No. of Consumer Testers | 78 | 79 | 122 | 125 | 75 | 75 |
| Overall Opinion (Excellent/Very Good) | 57% | 40% | 54% | 53% | 69% | 55% |
| Comparison to Usual Product-- Much Better Body | 19% | 13% | 13% | 20% | 31% | 26% |
| Total Body (Much Better/Better) | 47% | 27% | 45% | 44% | 56% | 50% |
| Just Right Body | 73% | 71% | 65% | 74% | 81% | 76% |
| Right Amount of Conditioning | 57% | 58% | 60% | 57% | 66% | 69% | the formulation of Example 4 contains no polymer. Example 4 was included to demonstrate the surprising results obtained when cationic polymer was added to the high pH formulation.

One skilled in the art viewing the data relative to Examples 1, 3 and 4 in Table 2 would expect that increasing the pH from an acidic pH to an alkaline pH, with or without polymer, would have no real bodifying effect on fine hair. Indeed, this is observed when the data obtained from the use of Examples 1, 3 and 4 are compared. Also, adding a cationic polymer to the acidic shampoo formulation resulted in a decline in bodifying action as perceived by the users (compare Example 2 versus Example 1).

However, the inclusion of a cationic polymer in the alkaline pH formulation, as represented by the formulation of Example 5, surprisingly and unexpectedly produced a product having attributes favorable to 69% of the test population ("overall opinion"), and a particularly high rating for bodifying action (i.e., "just right body—81%; "total body"—56%). In virtually all of the categories in Table 2, the alkaline formulation containing cationic polymer surprisingly surpassed all of the other test formulations in achieving a favorable opinion of the perception of increased body by the users. These results are particularly surprising and unexpected since, prior to the present invention, a cationic polymer at alkaline pH was not known to possess any bodifying capabilities.

The inclusion of a nonionic polymer in the alkaline shampoo formulation (Example 6) demonstrated a trend toward an improvement in bodifying action and an increase in favorable attributes to the users, compared with the alkaline formulation without polymer and with the acidic formulations.

In sum, the Table 2 data reveal that pH had no real effect on the perception of increased body in the formulations without polymer. Cationic polymer in a formulation at acidic pH resulted in a general deterioration in the perception of increased body. Surprisingly, the formulation at alkaline pH containing a cationic polymer resulted in a product with a profound increase in the perception of body by the user. Until the present invention, it was neither recognized nor appreciated that a cationic polymer in an alkaline formulation was stable and caused an increase in bodifying action on the hair.

The acidic and alkaline formulations presented in Examples 1–6 contain an anionic/amphoteric surfactant blend that is generally used in compositions of this type. In these formulations, the surfactant blend used was the same, but the amount of surfactant was varied so that the final product was stable in either the acidic or the alkaline pH environment of the product. It will be appreciated by those having skill in the art that stability of a product is a key criterion to attain prior to the initiation of consumer use testing. By stability is meant maintaining a homogeneous solution.

More specifically in this regard, nonionic polymers are not tolerant of high surfactant levels due to their competition for free water with ethoxylated surfactant. Thus, the use of lower levels of surfactant was necessary to achieve a stable product. Cationic polymers, on the other hand, can tolerate higher levels of surfactant in some formulations (e.g., acidic), but not in others (e.g., alkaline).

Examples 1–3

Acidic pH Formulations

The pH of the acidic shampoo formulations presented in Examples 1–3 (and as tested in Table 2) was between 5.0 and 6.0, which is typical of formulations of this type. Variation is expected on a batch-to-batch basis both above and below the expected pH range. The pH of the acidic/no polymer formulation of Example 1 was somewhat lower than the typical range because it was a production batch that had aged; thus, a slight downward trend in pH was both expected and acceptable based on stability data.

Example 1

| No Polymer, pH 4.74 | |
| --- | --- |
| {PRIVATE}INGREDIENT (CTFA NAME) | Wt % |
| Surfactant blend | 60.1 |
| Citric acid | 0.15 |
| Cocamide MEA | 0.5 |
| Preservative | 0.2 |
| Fragrance | 0.75 |
| Colorant | 0.0004 |
| Deionized (DI) Water | QS 100 |

Example 2

| Cationic Polymer, pH 5.50 | |
|---|---|
| {PRIVATE}INGREDIENT (CTFA NAME) | Wt % |
| Surfactant blend | 60.1 |
| Citric acid | 0.08 |
| Cocamide MEA | 2.0 |
| Preservative | 0.105 |
| Fragrance | 0.75 |
| Sodium chloride | 0.35 |
| Guar hydroxypropyltrimonium chloride | 0.15 |
| DI Water | QS 100 |

Example 3

| Nonioimic Polymer, pH 5.60 | |
|---|---|
| {PRIVATE}INGREDIENT (CTFA NAME) | Wt % |
| Surfactant blend | 47.0 |
| Citric acid | 0.02 |
| Lauramide DEA | 3.00 |
| Preservative | 0.05 |
| Fragrance | 0.85 |
| PEG-7M | 0.30 |
| DI Water | QS 100 |

Examples 4–6

Alkaline pH Formulations

The alkaline shampoo formulations presented in Examples 4–6 were prepared in accordance with the present invention and have a pH between 8.5 and 9.5. As described above for the acidic formulations, variation is expected on a batch-to-batch basis both above and below the expected pH range.

Example 4

| No Polymer, pH 9.20 | |
|---|---|
| {PRIVATE}INGREDIENT (CTFA NAME) | Wt % |
| Surfactant blend | 60.1 |
| Citric acid | 0.02 |
| Lauramide DEA | 3.00 |
| Preservative | 0.15 |
| Fragrance | 0.75 |
| DI Water | QS 100 |

Example 5

| Cationic Polymer, pH 8.75 | |
|---|---|
| {PRIVATE}INGREDIENT (CTFA NAME) | Wt % |
| Surfactant blend | 47.00 |
| Citric acid | 0.02 |
| Aminomethyl propanol (AMP) | 0.10 |
| Cocamide MEA | 1.30 |
| Sodium chloride | 0.25 |
| Fragrance | 0.75 |
| Guar hydroxypropyltrimonium chloride | 0.10 |
| DI Water | QS 100 |

Example 6

| Nonionic Polymer, pH 8.86 | |
|---|---|
| {PRIVATE}INGREDIENT (CTFA NAME) | Wt % |
| Surfactant blend | 47.00 |
| Citric acid | 0.02 |
| Aminomethyl propanol (AMP) | 0.10 |
| Cocamide MEA | 1.30 |
| Sodium chloride | 0.25 |
| Fragrance | 0.75 |
| PEG-7M | 0.30 |
| DI Water | QS 100 |

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. It is therefore to be understood that within the scope of the appended claims, the invention may be practiced otherwise than as specifically described.

What is claimed is:

1. An aqueous composition stable over time and adapted for application to hair, comprising at least one nonionic poly(ethylene oxide) homopolymer, at least one anionic surfactant present in an amount of about 1% to about 50% active, and water in an amount of about 30% to about 95%, by weight, based on the total weight of the composition; the composition having a pH of above 8 to about 14, the nonionic homopolymer being present in the composition in an amount sufficient to increase the perception of hair body and fullness when the composition is applied to hair, compared with a like composition not containing the nonionic homopolymer.

2. The composition according to claim 1, wherein the nonionic homopolymer has the structure:

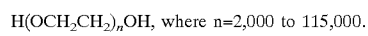

$H(OCH_2CH_2)_nOH$, where n=2,000 to 115,000.

3. The composition according to claim 2, wherein the nonionic homopolymer is selected from the group consisting of PEG-2M, PEG-5M, PEG-7M, PEG-14M, PEG-9M, PEG-14M, PEG-20M, PEG-23M, PEG-45M and PEG-115M.

4. The composition according to claim 1, wherein the nonionic homopolymer is present in the composition at about 0.01% to about 10%, by weight, based on the total weight of the composition, and wherein the pH of the composition is from above 8 to about 10.

5. The composition according to claim 1, wherein the anionic surfactant is a straight chain or branched chain alkyl or alkyl aryl sulfate or sulfonate having from 8 to 22 carbons in the alkyl radical, the anionic surfactant being optionally ethoxylated with from 1 to 5 mols of ethylene oxide (EO) per molecule.

6. The composition according to claim 1, wherein the anionic surfactant is selected from the group consisting of sodium cetyl sulfate, sodium myristyl sulfate, sodium lauryl sulfate, sodium tallow sulfate, sodium dodecyl sulfate, sodium decylbenzene sulfonate, sodium tridecylbenzene sulfonate, sodium $C_{14}$–$C_{16}$ olefin sulfonate, sodium $C_{12}$-$C_{15}$ alcohol sulfate, sodium lauryl ether sulfate, sodium myristyl ether sulfate, sodium polyoxyethylene (5 mols EO) lauryl ether sulfate, sodium polyoxyethylene (12 mols EO) lauryl ether sulfate, sodium nonylphenyl ether sulfate, sodium polyoxyethylene (1 to 4 mols EO), $C_{12}$–$C_{15}$ alkyl ether sulfate, sodium lauryl sulfoacetate and mixtures thereof.

7. The composition according to claim 1, further comprising an amphoteric surfactant.

8. The composition according to claim 7, wherein the amphoteric surfactant is selected from the group consisting of N-alkyl-β-imino dipropionates and basic ammonium compounds derived from 2-alkyl-substituted imidazoline.

9. The composition according to claim 4, wherein the nonionic homopolymer has the structure:

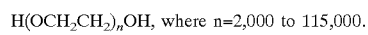

$H(OCH_2CH_2)_nOH$, where n=2,000 to 115,000.

10. The composition according to claim 9, wherein the nonionic homopolymer is selected from the group consisting of PEG-2M, PEG-5M, PEG-7M, PEG-14M, PEG-9M, PEG-14M, PEG-20M, PEG-23M, PEG-45M and PEG-115M.

11. The composition according to claim 9, wherein the anionic surfactant is a straight chain or branched chain alkyl or alkyl aryl sulfate or sulfonate having from 8 to 22 carbons in the alkyl radical, the anionic surfactant being present in an amount of from about 5% to about 35% active, and optionally ethoxylated with from 1 to 5 mols of ethylene oxide (EO) per molecule.

12. A method to impart to an individual a perception of fullness, body and texture to fine or very fine hair, comprising: applying a hair fullness, body and texture-increasing amount of the composition of claim 1 to the hair and rinsing the hair.

13. The method according to claim 12, wherein the composition is applied to the hair for about 30 to 60 seconds prior to rinsing the hair.

* * * * *